United States Patent
Marshall et al.

(10) Patent No.: US 11,045,266 B2
(45) Date of Patent: *Jun. 29, 2021

(54) LOAD CELLS IN AN INSTRUMENT DRIVE

(71) Applicant: CMR Surgical Limited, Cambridge (GB)

(72) Inventors: Keith Marshall, Cambridge (GB); Nikki Priyam Su-Ling Phoolchund, Cambridge (GB); Thomas Bates Jackson, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,734

(22) Filed: Apr. 14, 2020

(65) Prior Publication Data

US 2020/0281668 A1 Sep. 10, 2020

Related U.S. Application Data

(63) Continuation of application No. 15/563,839, filed as application No. PCT/GB2016/051079 on Apr. 20, 2016, now Pat. No. 10,653,487.

(30) Foreign Application Priority Data

Apr. 21, 2015 (GB) ..................................... 1506710

(51) Int. Cl.
| | | |
|---|---|---|
| *G01G 1/22* | (2006.01) | |
| *A61B 34/30* | (2016.01) | |
| *F16C 19/52* | (2006.01) | |
| *G01L 1/22* | (2006.01) | |
| *B25J 13/08* | (2006.01) | |
| *G01L 5/00* | (2006.01) | |
| *G01L 1/04* | (2006.01) | |
| *A61B 34/00* | (2016.01) | |

(Continued)

(52) U.S. Cl.
CPC .............. *A61B 34/30* (2016.02); *A61B 34/77* (2016.02); *B25J 13/085* (2013.01);
(Continued)

(58) Field of Classification Search
CPC ............ A61B 2562/164; G01L 1/2237; G01L 1/2231; G01L 1/2243; G01L 1/2225; G01L 1/2218
See application file for complete search history.

(56) References Cited

U.S. PATENT DOCUMENTS 9,859,774 B2    1/2018  Klinke et al.
10,653,487 B2 * 5/2020  Marshall .............. G01L 1/2237
(Continued)

FOREIGN PATENT DOCUMENTS

CN    101044381    9/2007
CN    102036869    4/2011
(Continued)

OTHER PUBLICATIONS

First Office Action related to CN201680022604.3, dated Mar. 21, 2019.
(Continued)

*Primary Examiner* — Richard W Ridley
*Assistant Examiner* — Brian J McGovern
(74) *Attorney, Agent, or Firm* — Renner, Otto, Boisselle & Sklar, LLP

(57) ABSTRACT

A drive unit for providing drive from a robot arm to an instrument comprises a plurality of drive elements for engaging corresponding elements of the instrument, and a load cell structure. Each drive element is movable along a drive axis and the drive axes of each of the drive elements are substantially parallel to each other. The load cell structure includes a plurality of deflectable bodies coupled to the drive elements for sensing load on the drive elements parallel to their drive axes, and a frame. The frame includes an integral member supporting the deflectable bodies in such a way as to isolate each deflectable body from the load applied to the or each other deflectable body.

15 Claims, 6 Drawing Sheets

(51) Int. Cl.
  *A61B 17/00* (2006.01)
  *A61B 90/00* (2016.01)
(52) U.S. Cl.
  CPC .............. *F16C 19/522* (2013.01); *G01L 1/04* (2013.01); *G01L 1/2231* (2013.01); *G01L 1/2237* (2013.01); *G01L 1/2268* (2013.01); *G01L 5/0019* (2013.01); *A61B 2017/00477* (2013.01); *A61B 2090/064* (2016.02); *A61B 2562/164* (2013.01); *F16C 2361/61* (2013.01); *G01L 5/009* (2013.01)

(56) References Cited

U.S. PATENT DOCUMENTS

| | | |
|---|---|---|
| 2005/0224278 A1 | 10/2005 | Segawa |
| 2009/0249910 A1 | 10/2009 | Erikson et al. |
| 2013/0165854 A1 | 7/2013 | Sandhu et al. |
| 2013/0172713 A1 | 7/2013 | Kirschenman |
| 2014/0318299 A1 | 10/2014 | Oyola et al. |
| 2015/0374449 A1 | 12/2015 | Chowaniec et al. |

FOREIGN PATENT DOCUMENTS

| | | |
|---|---|---|
| EP | 1015944 B1 | 2/2013 |
| WO | 2013159776 | 10/2013 |

OTHER PUBLICATIONS

English translation of First Office Action related to CN201680022604.3, dated Mar. 21, 2019.

Examination Report dated Mar. 23, 2021, for corresponding Indian Patent Application No. 201717040308.

* cited by examiner

LOAD CELLS IN AN INSTRUMENT DRIVE

This application claims priority to U.S. patent application Ser. No. 15/563,839 filed on Oct. 2, 2017, which claims benefit of International Patent Application No. PCT/GB2016/051079 filed on Apr. 20, 2016, and published in the English language, both of which are hereby incorporated herein by reference.

BACKGROUND OF THE INVENTION

This invention relates to sensing loads in a mechanical interface between a surgical robot arm and a surgical instrument.

In designing a robot arm for performing surgical procedures, one desirable characteristic is for the arm to be relatively small and light-weight. These characteristics provide a number of advantages: for example that the arm is easier for a technician to position before surgery takes place, that more arms can be fitted closely together around a surgical site, and that the forces required to move the arms are less than with bulkier devices. It is particularly desirable to reduce size and weight at the distal end of the arm. Since instruments are normally attached at the distal end of the arm, that implies reducing the size and weight of the arm-to-instrument interface.

Instruments for use in robotic surgery may have various mechanical elements which can be moved under the control of the robot. The interface provided on the arm may include on its exterior one or more movable mechanical elements which can couple to corresponding elements on the instrument when the instrument is in place on the interface. Those movable elements on the arm can be driven by motors or other actuators in the arm, and that motion can be transferred through the interface to the corresponding elements on the instrument. In that way the mechanical elements on the instrument can be driven from the arm. It is desirable for the control system of the robot to be able to receive feedback on the position of the mechanical drive to the instrument and on the force being applied through that drive. One way to do this is to provide one or more force sensors on the arm-to-instrument interface.

A difficulty with providing such sensors is that first they should be small and light, so as to avoid making the arm more bulky; but also, since the forces applied in surgery can be relatively small, they should be relatively sensitive and accurate. This requires careful design of the sensors. In addition, when multiple sensors are provided to sense force on multiple force paths it is desirable for the arrangement to avoid force on one path influencing the measurement on another path.

FIG. 1 shows one possible arrangement for sensing force in an instrument drive of a surgical arm. A motor 1 is attached to a lead screw 2, so that the motor can rotate the lead screw about its axis. The shaft of the lead screw comprises a threaded portion 3 and a non-threaded portion 4. Bearings 5, 6 are bonded to the non-threaded portion in such a way that they cannot slide along the shaft. A follower nut 8 is threaded onto the lead screw. The follower nut is restrained, for example by running in a slot defined in an exterior wall of the arm, so that it cannot rotate when the lead screw is turned by the motor. As a result, turning the lead screw 2 by means of the motor 1 results in the follower nut 8 translating along the axis of the lead screw. The follower nut has a formation 9 which can mate with a corresponding formation on an instrument in order to drive motion of a part of the instrument when the instrument is fixed to the surgical arm.

A load cell 7 is located between the bearings 5, 6. The load cell is shown in more detail in FIG. 2. The load cell comprises an annular outer housing 10. A membrane 11 is suspended across the interior of the housing. Strain gauges 13, 14 are fixed to the membrane so as to sense distortion of the membrane. The strain gauges provide an electrical output indicative of the strain on the membrane. At the centre of the membrane is a hole 12. Load cells for this type are commercially available, for example the Emsyst EMS 70. Other types of load cell include the FOWA-1 annular load cell from Muller Industrie-Elektronik GmbH. These load cells are used for applications like measuring cable tension or bolt compression.

When the load cell is attached to the instrument drive of FIG. 1 the membrane is held between the bearings 5, 6, with the shaft of the lead screw passing through hole 12. The housing 10 is attached to the body of the robot arm. In this way, the lead screw is at least partially supported from the body of the robot arm by the load cell 7. When a force is applied from an instrument along the axis of the lead screw, that force is transmitted through formation 9 to the follower nut 8. The pitch of the thread of the lead screw is such that the axial force does not cause the lead screw to rotate. Instead the force is transmitted by the bearings 5, 6, which are longitudinally fast with the lead screw, to the membrane of the load cell. That force can then be detected by the strain gauges 13, 14. This provides an indication of the force applied by the instrument.

In order to drive all the motions of a more complex instrument the robot arm can have a number of such instrument drives. As shown in FIG. 1, the load cell can be the most radially prominent part of the instrument drive. Improving the packaging of the load cell can therefore contribute to the compactness of the arm-to-instrument interface. When the interface has a number of drives of the type shown in FIG. 1, one way to package them efficiently is to stagger the drives so that the load cell of each drive is offset longitudinally from the load cell(s) of adjacent drive(s). However, a disadvantage of this is that it tends to increase the overall length of the instrument drive assembly.

There is a need for an improved drive assembly for a surgical robot arm.

BRIEF SUMMARY OF THE INVENTION

According to the present invention there is provided a drive unit for providing drive from a robot arm to an instrument, the drive unit comprising: a plurality of drive elements for engaging corresponding elements of the instrument, each drive element being movable along a drive axis and the drive axes of each of the drive elements being substantially parallel to each other; and a load cell structure comprising a plurality of deflectable bodies coupled to the drive elements for sensing load on the drive elements parallel to their drive axes, and a frame comprising an integral member supporting the deflectable bodies in such a way as to isolate each deflectable body from load applied to the or each other deflectable body.

The drive unit may comprise a plurality of lead screws, each of the drive elements being in threaded interengagement with a respective one of the lead screws. The frame may define a set of apertures, the lead screws may extend through the apertures and the deflectable bodies may extend across the apertures from the frame to the lead screws.

Each deflectable body may be coupled to the respective lead screw via at least one bearing configured to permit the respective lead screw to rotate freely about its longitudinal axis with respect to the respective deflectable body.

The frame may extend generally perpendicularly to the lead screws or to other actuators for moving the drive elements relative to the remainder of the arm. The deflectable bodies may lie within the perimeter of the frame, at least when they are in their undeformed condition.

The deflectable bodies may be disposed side-by-side in a plane perpendicular to the drive axes of the drive elements.

The deflectable bodies may be substantially planar. The deflectable bodies may extend perpendicular to the drive axes of the drive elements.

The deflectable bodies may be substantially coplanar.

The frame may be substantially rigid. The frame may be configured so as to isolate each deflectable body from motion of the other(s).

The frame may be integral with the deflectable bodies.

Each of the deflectable bodies may be coupled to one or more strain gauges for sensing deflection of that deflectable body.

According to a second aspect of the present invention there is provided a drive unit as set out above, comprising: a plurality of motors for driving the drive elements to move; and a rigid housing supporting the drive elements and the motors, the housing comprising two components, a first component to which the motors are attached and a second component within which the drive elements are movable, the load cell structure being sandwiched between the first component and the second component.

The second component of the housing may be configured to prevent rotation of the drive elements about their drive axes.

There may be a splined coupling between each motor and a respective one of the lead screws, each splined coupling being configured to permit axial play between the respective motor and the respective lead screw. The splined coupling may be an Oldham coupler.

According to a third aspect of the present invention there is provided a surgical robot comprising a drive unit substantially as set out above.

The surgical robot may have a mobile arm comprising the drive unit and a surgical instrument engaged with the arm, the instrument comprising the said corresponding elements and the said corresponding elements being engaged with the drive elements so as to be driven thereby.

BRIEF DESCRIPTION OF THE DRAWINGS

The present invention will now be described by way of example with reference to the accompanying drawings.

DETAILED DESCRIPTION

In the surgical arm to be described below motion is transferred from the arm to parts of an instrument attached to the arm. To transfer the motion, movable members on the arm link mechanically to members on the instrument. The members on the arm are movable linearly by motors comprised in the arm. The members on the instrument are operatively coupled to joints by which elements of the instrument can be moved. The members on the arm are moved by a set of parallel lead screws, pistons or other linear actuators. Multiple ones of the actuators are attached to a common load cell unit. The load cell unit is an integral element which provides load sensing for all those multiple ones of the actuators. The load cell unit comprises a set of sensor structures, one for each of those actuators, and a unitary isolation wall which joins the sensor structures together and also isolates each sensor structure mechanically from the other(s). The isolation wall extends generally perpendicular to the motion of the linear actuators. The sensor structures are within the perimeter of the isolation wall. In this way the sensor structure can be made particularly compact.

Figure 1:
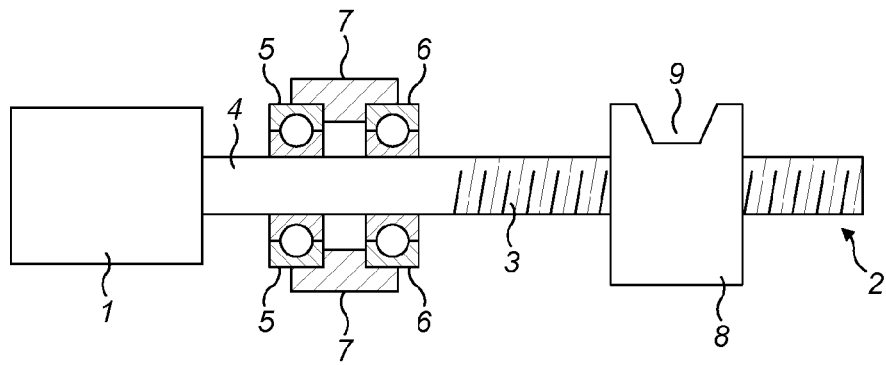
FIG. 1 illustrates a drive mechanism for a surgical robot arm.
Figure 2:
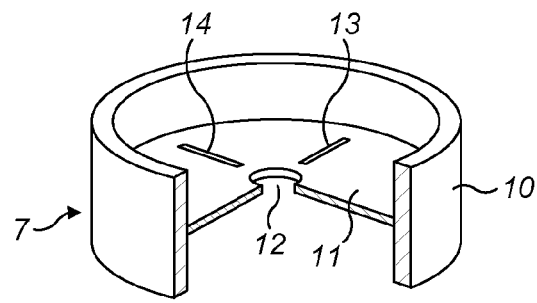
FIG. 2 illustrates a load cell for a surgical robot arm.
Figure 3:
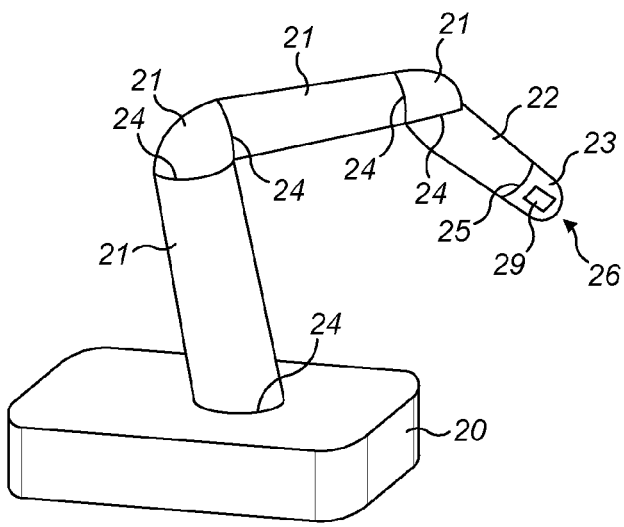
FIG. 3 shows a surgical arm.
Figure 5:
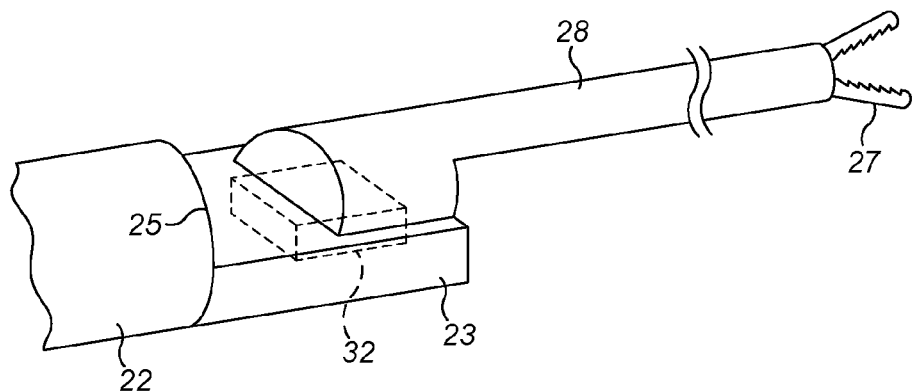
FIG. 5 shows an instrument attached to the instrument mount of FIG. 4.

FIG. 3 shows the arm of a surgical robot. The arm has a base 20 which can be positioned at a suitable location near an operating table for performing a surgical procedure on a patient. The arm has a number of rigid members or segments 21, 22, 23 along its length, and a number of joints 24, 25 which allow the rigid members to be moved relative to each other to position the distal end 26 of the arm in a desired location. The distal segment of the arm is designated 23, and the next most distal segment is designated 22. An instrument can be mounted to the distal end of the arm, as is shown in FIG. 5. In this example, the instrument comprises an end effector 27 at the distal end of an elongate shaft 28. In use, the instrument can be passed into the body of a patient and a surgical task can be performed by means of the end effector. A surgeon can operate the joints of the robot and the end effector from an operating station which is communicatively linked to motors and position/force sensors provided at the joints of the arm and in the arm-to-instrument interface.

Figure 4:
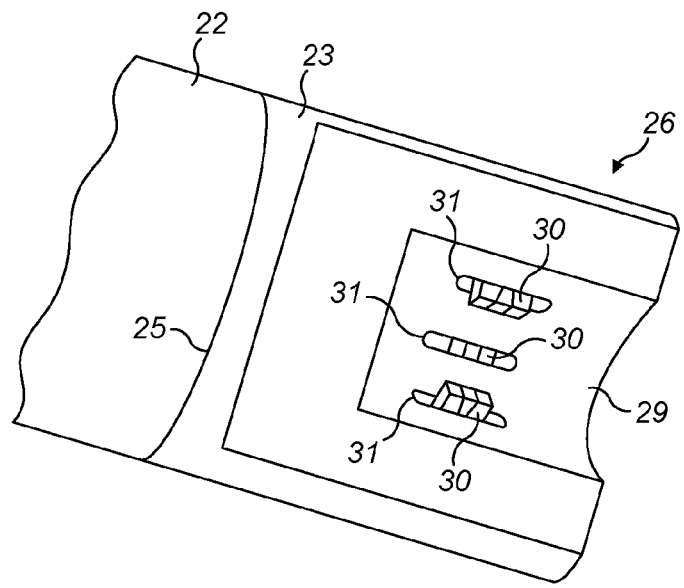
FIG. 4 shows the instrument mount of the arm of FIG. 3.

FIG. 4 shows the distal end 26 of the arm in more detail. The terminal member 23 of the arm is attached to the penultimate member 22 of the arm by a wrist joint 25. In this example the wrist joint is a simple rotational joint, but it could be a more complex arrangement, for example as described in our co-pending application PCT/GB2014/053523. Terminal member 23 defines an interface whereby an instrument can be attached to the arm. The interface comprises a channel 29 of U-shaped cross-section. (See FIG. 6). The channel is configured to mate with the proximal end of a surgical instrument. A number of drive tabs 30 protrude into the channel. Each drive tab extends through a respective window 31 in the exterior wall of the arm. The windows are elongate parallel to each other. The direction of elongation of the windows is towards the distal tip of the arm. Inside the exterior wall of the arm a drive mechanism is provided for each drive tab, which can drive the respective drive tab along the length of its window. The drive tabs are configured and positioned so that when a tool is attached on the interface corresponding drive elements on the tool engage the drive tabs. Those elements on the tool are linked to movable external elements on the tool, for example the jaws of the end effector 27 of FIG. 5 or a joint that permits the shaft of the tool to be redirected. Thus, when the tool is fixed in place on the interface the movable external elements of the tool can be caused to move by operation of the drive mechanisms in the arm. Each drive element on the tool could be attached to a flexible fibre which runs inside the shaft of the tool and is then coupled to a respective one of the movable external elements. In that way, when the drive tab on the arm is moved, that causes a drive element coupled to it to move, the fibre coupled to that drive element is in turn moved, and that causes the movable component of the instrument to move.

Figure 6:
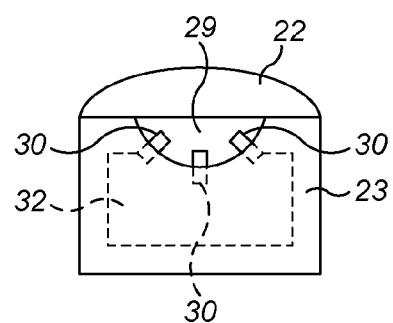
FIG. 6 is an end view of the instrument mount of FIG. 4.
Figure 7:
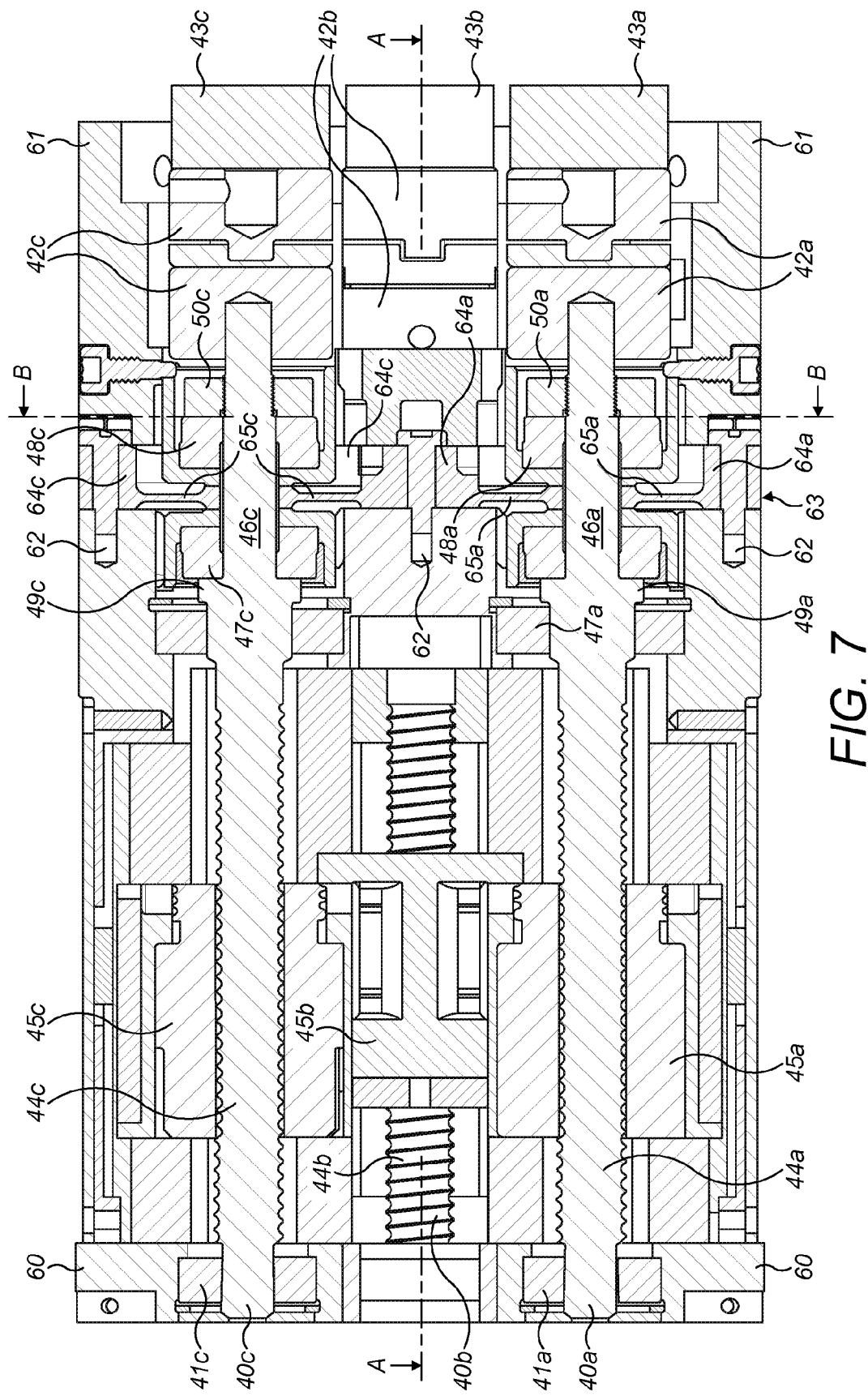
FIG. 7 is a plan view of a drive mechanism of the instrument mount of FIG. 4.
Figure 8:
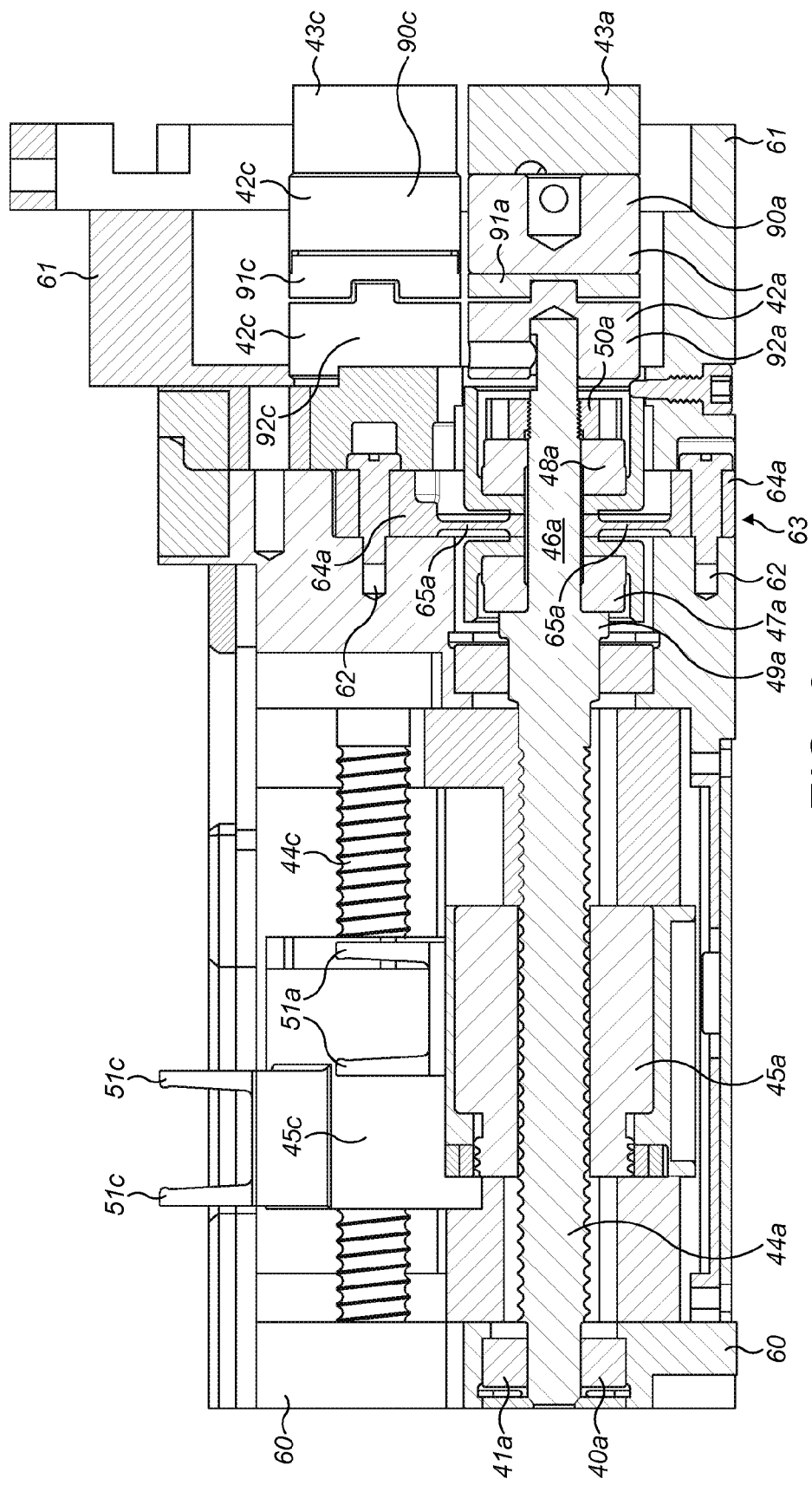
FIG. 8 is a cut-away side view of the drive mechanism of FIG. 7 on line A-A.
Figure 9:
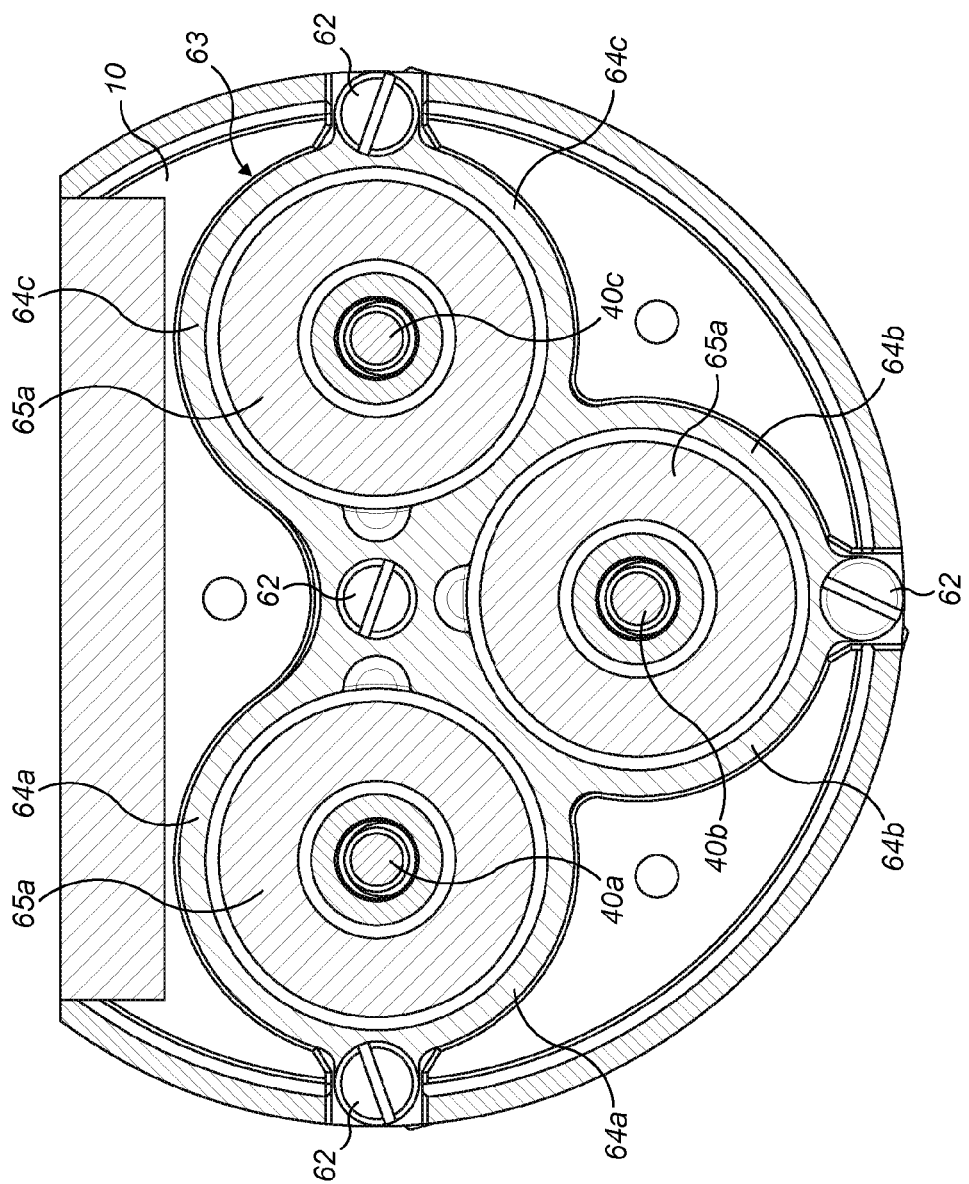
FIG. 9 is a cut-away end view of the drive mechanism of FIG. 7 on line B-B.

FIG. 6 is an end view of the distal end of the arm. FIG. 6 shows that inside the distal member 23 of the arm there is a drive unit 32. Drive unit 32 comprises the drive mechanisms for causing the drive tabs 30 to move. The drive unit is shown in detail in FIGS. 7 to 9.

The drive unit comprises three independently operable drive mechanisms for driving three drive tabs. In the explanation below, analogous components of each drive mechanism will be designated by the same reference number, with the suffixes "a", "b" and "c" identifying the parts of the three drive mechanisms respectively.

Each drive mechanism comprises a lead screw 40. One end of the lead screw is supported by an end bearing 41. The other end of the lead screw is rotationally fast with a multi-part motor coupler 42 which couples the lead screw to an electric motor 43. In this example the coupler is an Oldham coupler. One purpose of the coupler 42 is to accommodate any small radial offset between the rotation axes of the motor and the lead screw. A major portion 44 of the lead screw is threaded. A follower nut 45 runs on the threaded portion. The nut 45 is internally threaded and mates threadedly with the lead screw. A further portion 46 of the lead screw is smooth-sided. Two bearings 47, 48 are attached to the smooth-sided portion 46 in such a way that they are axially fast with the lead screw. The bearings 47, 48 could be fixed to the lead screw with adhesive, or pinched between a radially outwardly extending shoulder formation 49 on the lead screw and a locking nut 50 which is threaded on to the lead screw. The follower nut 45 carries a formation 51 (FIG. 8) which constitutes the drive tab. Formation 51 is configured for mating with a corresponding formation on a surgical instrument to drive the formation on the instrument to move back and forth along the axis of the lead screw.

Bearings 41 are supported by a body block 60 of the drive mechanism. Motors 43 are supported by an end block 61 of the drive mechanism. The body block 60 and the end block 61 are attached together by bolts (not shown) which pass through smooth-sided holes in the end block and into threaded holes in the body block.

Sandwiched between the body block and the end block is a combined load cell unit 63. The combined load cell unit is shown end-on in FIG. 9 and in various views in FIG. 10. The combined load cell unit 63 comprises a unitary body element which constitutes a substantially rigid frame and, integral with the frame, a set of somewhat flexible webs. The frame constitutes three annular rings 64a, 64b, 64c whose walls, when installed in the drive mechanism extend parallel with the axes of the lead screws. The rings are integral with each other. The webs 65a, 65b, 65c extend across the interiors of respective ones of the annular rings. At the centre of each web is a flange 66a, 66b, 66c and a through-hole 67a, 67b, 67c. When the combined load cell unit is installed in the drive mechanism a lead screw 40 passes through each through-hole 67, and the respective flange 66 is clamped between the respective bearings 47, 48. Packing cups may be interposed between the bearings and the load cell. Since the bearings 47, 48 are axially fast with the respective lead screw, the central part of the web 65 is also axially mounted to the lead screw; whereas the exterior part of the web is integral with the respective annular ring of the frame, which is held by bolts 62 to the body block of the frame.

Strain gauges 68 are bonded to the webs 65. Since the webs are thin, and somewhat flexible, a web can deflect when an axial load is applied on its flange 66 by the lead screw 40 that passes through that hole. That flexing can be sensed by the strain gauges 68, which provide an electrical output indicative of the axial load on the respective lead screw. Because the webs are isolated from each other by the substantially rigid annular rings 64, load on each lead screw can be sensed independently. Instead of webs the deflectable elements could be in the form of fingers or beams. The thicker and/or stiffer regions between the webs inhibit the propagation of force between webs, which reduces the risk of a measurement made by one strain gauge being corrupted by force from a force path associated with another strain gauge.

The frame of the load cell unit acts as a carrier for the three sensors corresponding to respective ones of the three lead screws. Integrating these by means of a single carrier in this way can help to save space.

The frame of the load cell unit is an integral structure formed of a unitary piece of material which supports the flexible elements 65 of all the three load cells. The material could be a metal, for example aluminium, or a polymer material. The frame is arranged so that the flexible elements are in the same plane as each other. The webs 65 are planar. The load cell unit is arranged so that the three webs 65 are coplanar. Because the three load cells are disposed side-by-side, in a common plane transverse to the rotation axes of the lead screws, the drive mechanism can be made particularly compact. Furthermore, the job of assembling the drive mechanism is made easier by the fact that the combined load cell unit can be assembled to, and attached to, the body block 60 of the drive mechanism as a single piece.

The frame that supports the webs 65 could itself be flexible. Since it is bolted to the body block 60 of the drive mechanism, the body block could be relied upon to stiffen the frame and isolate load on one web from the others.

As discussed above, the lead screws 44 are driven to rotate in order to convey linear motion to the followers 45. It is desirable for the load cells to be isolated from that rotation so that it does not influence their measurements of axial load on the lead screws. To that end, the flexible web 65 associated with each load cell is attached to the respective lead screw in the following manner. The flexible web has at its radially inward part a ring or flange 66 which is thicker than the flexible portion 65 of the web. The flange 66 is located between two bearings 47, 48. The proximal part 46 of the shaft of the lead screw passes through the bearings and the flange. The bearings are clamped firmly against the flange by virtue of their being trapped between a radial projection 49 of the lead screw and a clamping nut 50 which is threaded onto the lead screw and tightened to pack the bearings and the flange together. Each bearing permits free rotation of one of its axial faces with respect to the other, but is substantially incompressible in an axial direction. This means that when the lead screw rotates, the flange 66 and hence the web 65 is isolated from that rotation; whereas when the lead screw moves axially, that motion is passed faithfully to the flange so it can be measured as deformation of the web. The fact that the web is substantially isolated from rotary motion of the lead screw improves the accuracy of force measurement. The fact that the flange 66 is thicker than the web 65 means that the adjoining faces of the bearings 47, 48 are both spaced from the web. That permits the web 65 to deflect in the axial direction without impinging on the faces of the bearings.

The coupler 42 comprises three parts 90, 91, 92. (See FIG. 8). Parts 90 to 92 are disposed generally in series along the axial direction of each lead screw. Part 92 is attached rigidly to the lead screw. Part 90 is attached rigidly to the output shaft of motor 43. Part 91 is located between parts 90 and 92 and is splined to both so as to be able to convey rotation from part 90 to part 92. The splined joints between part 91 and parts 90/92 are arranged so as to permit play in the axial direction. This allows the lead screw to be driven in rotation whilst avoiding axial motion of the lead screw being corrupted by resistance from the motor 43. This improves measurement accuracy. At its distal end the lead screw can slide freely in an axial direction in bearing 41. To preserve a desired amount of axial play in the splined coupling the coupling can be assembled with spacers between its parts. The spacers can then be removed once the other parts have been set in place but before use. The coupler 42 could have three parts, as illustrated, two parts with a splined coupling between them, or more parts. The spline(s) may be of any suitable shape: for example radial projections/recesses as shown in the figures, castellations or axial pins that fit into corresponding holes in the mating part. The output shaft of the motor could be connected directly by a slidable splined coupling to the shaft of the lead screw; for example by the output shaft having an irregular cylindrical form and fitting into a corresponding keyway in the lead screw.

The body block 60 encloses the nuts 45 and partially encloses the configurations 51 for engaging the corresponding configurations of the instrument. The body bock may comprise configurations such as elongate walls or ribs which interact with the nuts 45 and/or the configurations 51 to prevent them from rotating relative to the block 60 when the lead screws are rotated.

Figure 10:
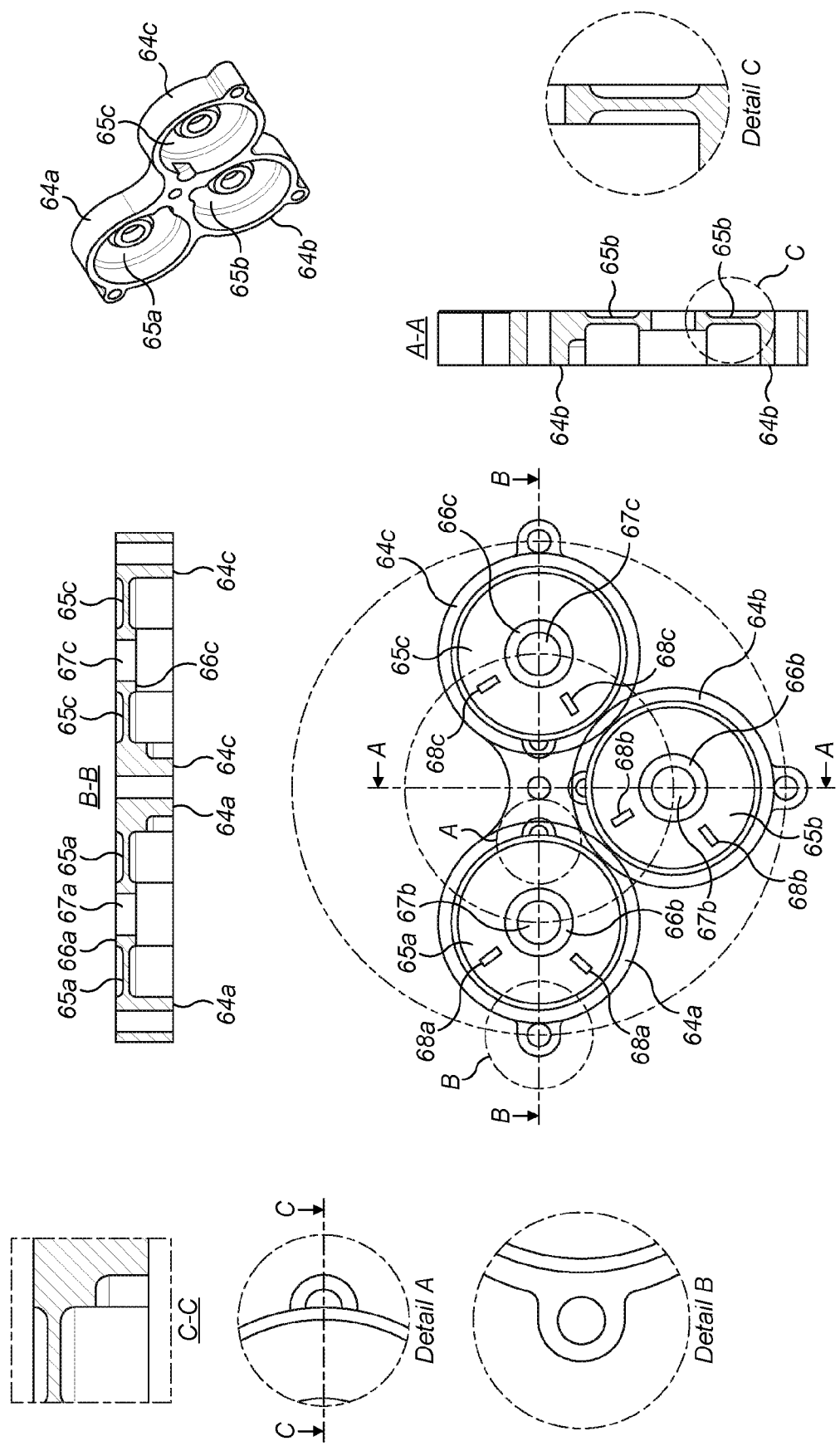
FIG. 10 illustrates a combined load cell housing.

In the load cell of FIG. 10 the webs are integral with the frame. In an alternative design the webs/membranes could be formed of separate components which are attached to the frame.

In the drive arrangement shown in the figures drive is transferred to the instrument and load is carried from the instrument to the load cell by the lead screws. Other approaches could be used to convey drive and load. For example, motors having pinions rotating about axes parallel to the plane of the webs could be mounted to the webs, for example by bolts passing through the flanged holes 67. The pinions of the motors could engage racks or other gears on the instrument.

As indicated above, the drive mechanism can be fitted in the arm of a robot, preferably in the distal segment of the robot, for providing a mechanical drive interface to an instrument. The robot could be a surgical robot. The instrument could be a surgical tool. For example, the instrument could be a cutting, grasping, imaging or irradiating tool.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A drive unit for providing drive from a robot arm to an instrument, the drive unit comprising:
    a plurality of drive tabs configured to engage corresponding elements of the instrument, each drive tab of the plurality of drive tabs being movable along a respective drive axis, and the respective drive axes of the plurality of drive tabs being substantially parallel to each other; wherein at least two of the respective drive axes are aligned along a first line and a third respective drive axis is positioned on a second line, the second line being parallel to and offset from the first line and
    a load cell structure configured to sense a load on the plurality of drive tabs parallel to the respective drive axes, the load cell structure including comprising:
    a plurality of membranes coupled to the plurality of drive tabs; and
    a frame supporting the plurality of membranes in such a way as to isolate each membrane of the plurality of membranes from the load applied to the or each other membrane of the plurality of membranes.

2. A drive unit as claimed in claim 1, wherein:
    the drive unit includes a plurality of lead screws, each of the plurality of drive tabs being in threaded interengagement with a respective one of the plurality of lead screws; and
    the frame defines a set of apertures, the plurality of lead screws extending through the set of apertures and the plurality of membranes extending across the set of apertures from the frame to the lead screws.

3. A drive unit as claimed in claim 2, wherein each of the plurality of membranes is coupled to a respective one of the plurality of lead screws via at least one respective bearing configured to permit the respective one of the plurality of lead screws to rotate freely about a respective one of the respective drive axes with respect to the membrane.

4. A drive unit as claimed in claim 1, wherein the plurality of membranes are disposed side-by-side in a plane perpendicular to the respective drive axes of the plurality of drive tabs.

5. A drive unit as claimed in claim 1, wherein the plurality of membranes are substantially planar and extend perpendicular to the respective drive axes of the plurality of drive tabs.

6. A drive unit as claimed in claim 1, wherein the frame is substantially rigid.

7. A drive unit as claimed in claim 1, wherein the frame is integral with the plurality of membranes.

8. A drive unit as claimed in claim 1, wherein each of the plurality of membranes is coupled to a respective strain gauge configured to sense deflection of the membrane of the plurality of membranes.

9. A drive unit as claimed in claim 1, further comprising:
    a plurality of motors configured to drive the plurality of drive tabs to move; and
    a rigid housing supporting the plurality of drive tabs and the plurality of motors, the housing including two components, a first component to which the plurality of motors are attached and a second component comprising apertures within which the plurality of drive tabs are movable, the load cell structure being sandwiched between the first component and the second component.

10. A drive unit as claimed in claim 9, wherein at least one of a wall or rib of the second component of the housing is configured to prevent rotation of the plurality of drive tabs about the respective drive axes.

11. A drive unit as claimed in claim 9, wherein:
the drive unit includes a plurality of lead screws, each of the plurality of drive tabs being in threaded interengagement with a respective one of the plurality of lead screws;
the frame defines a set of apertures, the plurality of lead screws extending through the set of apertures and the plurality of membranes extending across the set of apertures from the frame to the lead screws; and
the drive unit includes a respective splined coupling between each motor of the plurality of motors and a respective one of the plurality of lead screws, each splined coupling being configured to permit axial play between the motor of the plurality of motors and the respective lead screw of the plurality of lead screws.

12. A drive unit as claimed in claim 1, wherein the load cell structure comprises a plurality of flanges, each flange surrounding a respective one of the respective drive axes and being associated with a respective one of the plurality of membranes, wherein each membrane extends wholly across the area between the frame and a respective one of the plurality of flanges.

13. A surgical robot comprising the drive unit as claimed in claim 1.

14. A surgical robot as claimed in claim 13, wherein the drive unit is disposed at a distal end of the arm of the robot.

15. A surgical robot as claimed in claim 14, having a mobile arm that includes the drive unit and an instrument engaged with the arm, the instrument including corresponding elements engaged with the plurality of drive tabs so as to be driven thereby.

* * * * *